(12) United States Patent
López Rodríguez

(10) Patent No.: US 9,708,902 B2
(45) Date of Patent: Jul. 18, 2017

(54) BOREHOLE INSPECTION DEVICE AND SYSTEM WITH A SELF-CLEANING SYSTEM AND METHOD FOR LOADING EXPLOSIVES IN BOREHOLES

(75) Inventor: Jorge López Rodríguez, Vilafranca del Pendeés-Barcelona (ES)

(73) Assignee: MAXAMCORP HOLDING S.L., Madrid (ES)

( * ) Notice: Subject to any disclaimer, the term of this patent is extended or adjusted under 35 U.S.C. 154(b) by 605 days.

(21) Appl. No.: 13/977,306

(22) PCT Filed: Dec. 29, 2011

(86) PCT No.: PCT/EP2011/074204
§ 371 (c)(1),
(2), (4) Date: Oct. 10, 2013

(87) PCT Pub. No.: WO2012/089795
PCT Pub. Date: Jul. 5, 2012

(65) Prior Publication Data
US 2014/0022375 A1   Jan. 23, 2014

(30) Foreign Application Priority Data
Dec. 30, 2010 (EP) .................................... 10382367

(51) Int. Cl.
*H04N 9/47* (2006.01)
*H04N 7/18* (2006.01)
*E21B 47/00* (2012.01)
*F42D 1/22* (2006.01)
*G01N 21/15* (2006.01)
*G01N 21/954* (2006.01)

(52) U.S. Cl.
CPC ............ *E21B 47/0002* (2013.01); *F42D 1/22* (2013.01); *G01N 21/15* (2013.01); *G01N 21/954* (2013.01)

(58) Field of Classification Search
CPC ....................................................... E21B 47/00
USPC ............................................................ 348/85
See application file for complete search history.

(56) References Cited

U.S. PATENT DOCUMENTS

| 2,912,495 | A | * | 11/1959 | Moon ................. E21B 47/0002 348/85 |
| 2,940,370 | A |   | 6/1960 | Yandell |
| 3,244,085 | A | * | 4/1966 | Pulfer ...................... G01V 8/02 396/19 |
| 3,596,582 | A |   | 8/1971 | Sayer |
| 3,667,359 | A |   | 6/1972 | Watts et al. |

(Continued)

OTHER PUBLICATIONS

International Search Report, Mar. 20, 2012.

*Primary Examiner* — Jamie Atala
*Assistant Examiner* — Richard A Hansell, Jr.
(74) *Attorney, Agent, or Firm* — Tristan A. Fuierer; Moore & Van Allen, PLLC

(57) ABSTRACT

The present invention proposes a borehole inspection device, a borehole inspection system and a method for loading explosives in boreholes. The borehole inspection device comprises a tubular casing (7), illumination means (10) and image capturing means (9) housed in the casing (7), at least one circulation duct (16) for a fluid (4), and a diffusing element (1) suitable for spraying the fluid (4) circulating through the at least one circulation duct (16) onto a transparent closure (2) allowing the illumination and the image capture through it.

17 Claims, 7 Drawing Sheets

(56) References Cited

U.S. PATENT DOCUMENTS

| | | | | |
|---|---|---|---|---|
| 4,938,060 | A | * | 7/1990 | Sizer ........................ E21B 34/06 |
| | | | | 348/85 |
| 5,005,642 | A | * | 4/1991 | Moore ................. E21B 17/1021 |
| | | | | 166/241.5 |
| 5,419,188 | A | * | 5/1995 | Rademaker ........... E21B 17/203 |
| | | | | 367/35 |
| 6,041,860 | A | * | 3/2000 | Nazzal ................... E21B 23/002 |
| | | | | 166/250.01 |
| 6,091,546 | A | | 7/2000 | Spitzer |
| 6,397,754 | B1 | * | 6/2002 | Perlid ........................ F42D 1/10 |
| | | | | 102/312 |
| 7,792,552 | B2 | * | 9/2010 | Thomas ..................... 455/556.1 |
| 8,201,625 | B2 | * | 6/2012 | Almaguer ................ E21B 7/061 |
| | | | | 166/250.08 |
| 2003/0101156 | A1 | * | 5/2003 | Newman ........... G06F 17/30017 |
| 2007/0127780 | A1 | * | 6/2007 | Tawfiq ................ E21B 47/0002 |
| | | | | 382/109 |
| 2008/0021653 | A1 | * | 1/2008 | Kear ...................... G09B 23/40 |
| | | | | 702/11 |
| 2008/0143678 | A1 | * | 6/2008 | Sadler ................... G02B 27/017 |
| | | | | 345/168 |
| 2009/0038794 | A1 | * | 2/2009 | Yamate ................. E21B 47/123 |
| | | | | 166/254.2 |
| 2010/0265063 | A1 | * | 10/2010 | Eken ........................ F42D 5/02 |
| | | | | 340/539.32 |
| 2011/0185806 | A1 | * | 8/2011 | Pfutzner .................. G01V 7/06 |
| | | | | 73/152.54 |

* cited by examiner

A-B

BOREHOLE INSPECTION DEVICE AND SYSTEM WITH A SELF-CLEANING SYSTEM AND METHOD FOR LOADING EXPLOSIVES IN BOREHOLES

CROSS-REFERENCE TO RELATED APPLICATIONS

This application is filed under the provisions of 35 U.S.C. §371 and claims the priority of International Patent Application No. PCT/EP2011/074204 filed on 29 Dec. 2011 entitled "Borehole Inspection Device and System with a Self-Cleaning System and Method for Loading Explosives in Boreholes" in the name of Jorge LÓPEZ RODRÍGUEZ, which claims priority to European Patent Application No. EP 10382367.0, filed on 30 Dec. 2010, both of which are hereby incorporated by reference herein in their entirety.

TECHNICAL FIELD OF THE INVENTION

The invention is comprised in the technical field encompassing the methodologies for loading explosive in blast boreholes and/or those devices or tools which facilitates the control of correctly filling the explosive in the boreholes for the purpose of improving the safety and efficiency of the blast.

The present invention proposes a borehole inspection device and system which enable, by means of the novel design of its different parts, to be able to remain inside the borehole throughout the entire loading process sending real time images for viewing them in wireless binocular devices and/or for storing them in memory, by way of viewing glasses that the users would wear in the blast.

BACKGROUND AND PRIOR ART

The methodology today for controlling the process of filling the explosive load in boreholes is based on occasionally checking the fill level of the explosive with measuring tape, and on systematically checking the stemming, which is the final length of the borehole which is left free of explosive to be filled with an inert material that confines the energy developed by the explosive at the time of detonation.

There are usually working methodologies that typically gather the information provided in the drilling reports of boreholes, allowing, to a greater or lesser extent, the detection of problems related to the ground geology, such as the presence of voids intercepted by the boreholes, ground fractures, intercalation of lower/higher hardness strata, etc.

In the case of loaded boreholes considered to be problematic due to the mentioned geology, now it is usually mandatory to use cartridge formats, either factory cartridged or in situ packing in cartridges the bulk explosive. If any doubts come up, a check is performed by means of measuring tapes ballasted with a weight to verify that the explosive is correctly filling the volume of the borehole. In occasional cases, the boreholes are cased to prevent the leakage of explosive through ground fractures or caves. However, the uncertainty today while loading an explosive of a borehole has been inherent to it from the time there are no real time images of the filling process.

Concerning the inspection of blast boreholes by means of video cameras, today this is still an occasional, often marginal task because it hinders the normal loading process, because it is based on devices the designs of which do not allow a visual inspection while loading the explosive. The problems of the devices getting snagged inside boreholes and the dirt being deposited on the viewfinder of the cameras drastically reduce the operational efficiency in current inspection systems.

The cylindrical nature of a blast borehole is particularly and substantially different from that of any other type of conduit. The main difference is that these perforations are built to be filled with explosive and to later be destroyed in the process known as the blast process. When drilling a hole directly into the rock, almost always without protections or coatings on the borehole walls, which would greatly increase the cost and delay the blast process, falling rock or rock slides are very frequent and tend to trap any object that has been introduced in the borehole. Furthermore, the loading process itself already involves pouring or introducing the explosive, whereby objects frequently remaining inside the borehole are trapped.

SUMMARY OF THE INVENTION

The present invention solves the aforementioned problems by means of a borehole inspection device according to claim 1, a borehole inspection system according to claim 3 and a method for loading explosives in boreholes according to claim 14. The dependent claims define preferred embodiments of the present invention.

In a first inventive aspect, a borehole inspection device comprising a tubular casing, illumination means and image capturing means housed in the casing, at least one circulation duct for a pressurized fluid, and a diffusing element suitable for spraying the fluid circulating through the at least one circulation duct onto a transparent closure allowing the illumination and the image capture through it, is defined.

The borehole inspection device can be cleaned without needing to be extracted to the surface by means of a cleaning fluid driven from the exterior which is sprayed by means of a diffusing element onto the transparent viewfinder of the image capturing means located inside the borehole.

In a preferred embodiment, the borehole inspection device has an annular circulation duct.

Despite having been designed to solve the particular drawbacks of inspecting boreholes, the inspection device according to the first inventive aspect can be used in the inspection of other substantially tubular ducts in which there is a risk of a transparent element or viewfinder through which the image capture is performed becoming dirty.

In a second inventive aspect, a borehole inspection system comprising a borehole inspection device according to the first inventive aspect and a flexible tubular conduit, with certain torsional rigidity, internally housing fluid supply means and data transmission means, is defined.

In an advantageous embodiment, the borehole inspection device comprises a centering element deformable under the action of a force, which has shape memory and a double bend such that it allows correct centering of the inspection device inside the borehole, but which deforms in the event of an occasional stress, losing the double bend and resembling a tubular body, similar to the tubular conduit raising it from the surface. The centering element has an upper sector which, in a use situation, is in an upper position, substantially supported on the wall of the borehole, and a lower sector which, in a use situation, is in a lower position, substantially centered in the borehole. This design of the centering element also substantially improves the snagging risks.

The centering element is preferably arranged in a position between the inspection device and the tubular conduit, such that the lower sector of the centering element, substantially centered in the borehole in a use situation, also substantially keeps the inspection device centered.

In the context of the present invention, a position substantially centered in the borehole will be understood as that in which the image capturing means have a complete field of view of the section of the borehole. Likewise, self-cleaning will be understood as the operations which allow cleaning the transparent closure-viewfinder through which the images are captured, using a cleaning fluid supplied from outside the borehole, without needing to extract the equipment to the surface.

Nevertheless, the centering element can be longitudinally coupled, preventing the formation of projections, to the tubular conduit, partially or completely containing it, or being contained in a lower portion of the tubular conduit, the latter acquiring in both cases the shape with the double bend in the centering element due to its flexibility and both being connected to the borehole inspection device.

A rectifying element can be arranged between the centering element and the tubular conduit, allowing certain free rotation of the centering element about an axis substantially perpendicular to the axis of the borehole, the purpose of said rectifying element being to make the portion of the system downstream from the rectifying element independent so that it is not affected by a possible curvature memory of the tubular conduit.

In an advantageous embodiment, the cleaning fluid is preferably pneumatic, being able to incorporate different amounts of a cleaning fluid, to facilitate and enhance the cleaning action.

It is important to maximally reduce the unwanted problems of the equipment getting snagged inside boreholes. Consequently, the elements which are introduced in the borehole are joined together without considerable projections, such that the tubular conduit in the form of a hose raising the equipment from the surface and internally housing and protecting along the entire length of the borehole the conduits and wiring necessary for the images, illumination and cleaning fluid supply represents the maximum diameter of the components of the equipment introduced in the boreholes. Said tubular conduit has a series of rigid portions in its design which will allow and facilitate the inspection task.

In one embodiment, fiber optic conduits can be used as image capturing means and illumination means, which conduits are responsible for illumination, transmitting the light from the surface, and responsible for returning the image from inside the borehole to the surface for processing, said optical conduits being protected in their front part by the transparent closure.

In a preferred embodiment, the system comprises means for composing the captured images from inside the borehole with a value indicative of the depths of the borehole associated with the images, and a viewing system comprising wireless binocular glasses for viewing said composition. Advantageously, this embodiment will allow contemplating, analyzing and reproducing what takes place inside the borehole, knowing at what depth it is occurring, because a numerical value indicating the mentioned depth is integrated in the video image captured in real time. Furthermore, said wireless video viewing glasses give operators substantial mobility and allow them to avoid the typical drawbacks of conventional video display systems when they are used outdoors, in the open air.

The images and/or the depth readings can additionally or alternatively be recorded in a storage device for viewing them later.

In a third inventive aspect, a method for loading explosives in a borehole comprising inserting in a borehole a borehole inspection device of a borehole inspection system according to the second inventive aspect, loading the explosive in the borehole and capturing images from inside the borehole by means of the borehole inspection system while loading an explosive in the borehole, is defined.

The method for loading explosives in a borehole can comprise performing at least one cleaning operation onto the transparent closure of the borehole inspection device located inside the borehole.

In a preferred embodiment, the method for loading explosives in a borehole comprises viewing, while loading an explosive in the borehole, the images of loading the borehole together with a value indicative of the depths of the borehole associated with the captured images in a viewing system comprising wireless binocular glasses.

Advantageously, the method for loading boreholes of the invention allows the control of the loading process for loading the explosive inside the boreholes is based on the images and the information about the depth at which the device is located that can be viewed in real time by the process operators, being able to be recorded for later analyses. As a result of the advantageous design of the system, which prevents problems of snagging when it is introduced in and extracted from boreholes, allowing a rapid self-cleaning at all times without needing to extract the camera from the borehole, a centered view of the borehole and the viewing thereof is maintained at all times.

Regarding the efficiency of the use of the explosive, the simultaneous viewing of loading the explosive opens up enormous possibilities for optimally distributing the explosive. For example, being able to visually check, in real time while loading, the existence and the exact location of an intercalated stratum of little consistency (for example, clays), allows filling with an inert stemming material the area of influence of that soft stratum where the detonation gases would prematurely leak out without having done a useful job, then continuing with the explosive filling.

The efficiency of the use of the explosive is also improved by efficiently and rapidly solving problems of snagging cartridges. In known methods for loading explosives, the cartridges are launched one by one, the blaster checking with more or less skill if the cartridge correctly traverses a problematic area of the borehole by means of the sound the cartridge makes when it hits the bottom or the rest of the load. In the event that a cartridge is snagged, the means for recovering the cartridge today are very rudimentary and are based on blindly trying to hook onto the snagged cartridge. As a result of the device and system of the invention, the possibility of having images of the nature of the snagging will allow solving the drawback more safely and efficiently.

DESCRIPTION OF THE DRAWINGS

To complement the description that is being made and for the purpose of aiding to better understand the features of the invention according to a preferred practical embodiment thereof, a set of drawings is attached as an integral part of said description, in which the following has been depicted with an illustrative and non-limiting character.

DETAILED DESCRIPTION OF THE INVENTION

Figure 1A:
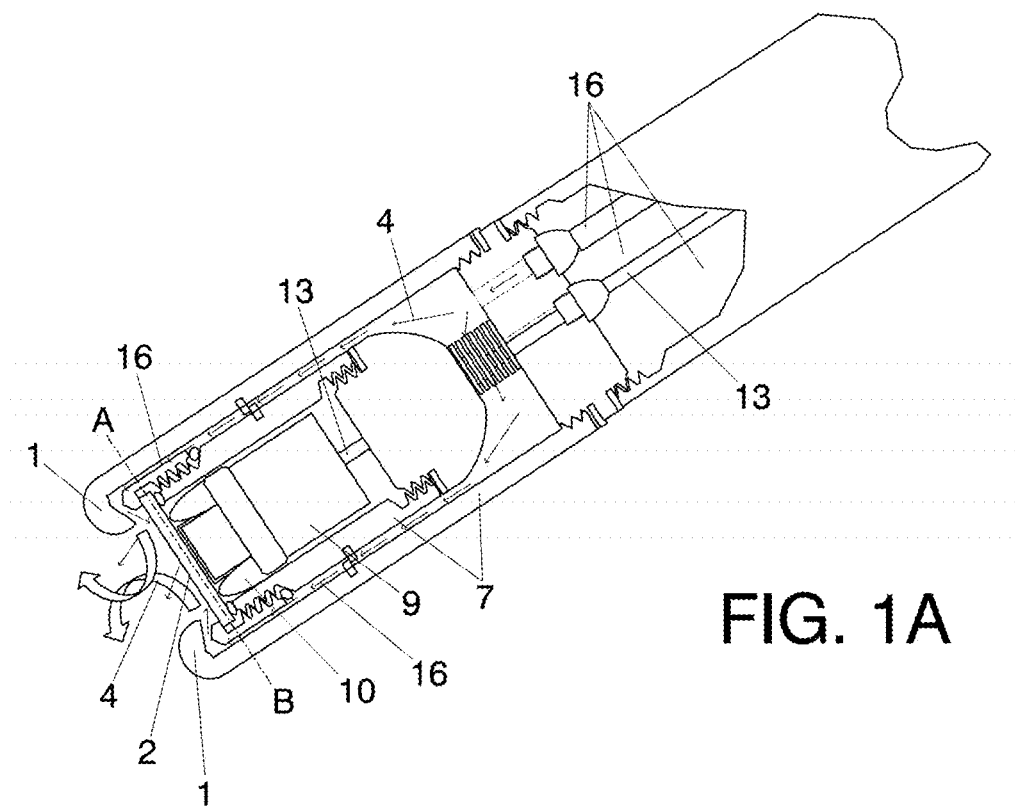
FIG. 1A shows a side section of the double body tubular casing comprised in the borehole inspection device of the invention.

FIG. 1A schematically shows a side section of a borehole inspection device according to the invention. A cylindrical casing (7) having a very small diameter with respect to the borehole, which keeps illumination means (10) for illuminating the borehole and image capturing means (9), for example, a camera, hermetically protected, can be seen in said figure. A diffusing element (1), preferably of the diffusing ring type, though it can be of any type which allows spraying a pressurized fluid, and the fluid circulation duct (16), are responsible for performing the self-cleaning operations without needing to extract the equipment to the surface, spraying on demand a cleaning fluid (4) supplied from the surface, onto the transparent closure (2) through which the borehole is illuminated and images of the borehole are captured. The transparent closure (2) can be cleaned occasionally for the purpose of removing any dirt remains deposited on said element, or by continuously spraying the fluid, therefore creating turbulences by way of an air lock, in order to prevent any foreign body from being deposited on said transparent closure (2).

In the embodiment shown, the cylindrical casing (7) has a double body, with an inner body and an outer body with certain clearance between them, suitable for the circulation of the cleaning fluid (4), thus configuring an annular circulation duct (16). However, one or several alternative circulation ducts, for example several different channels, could be configured.

Figure 1B:
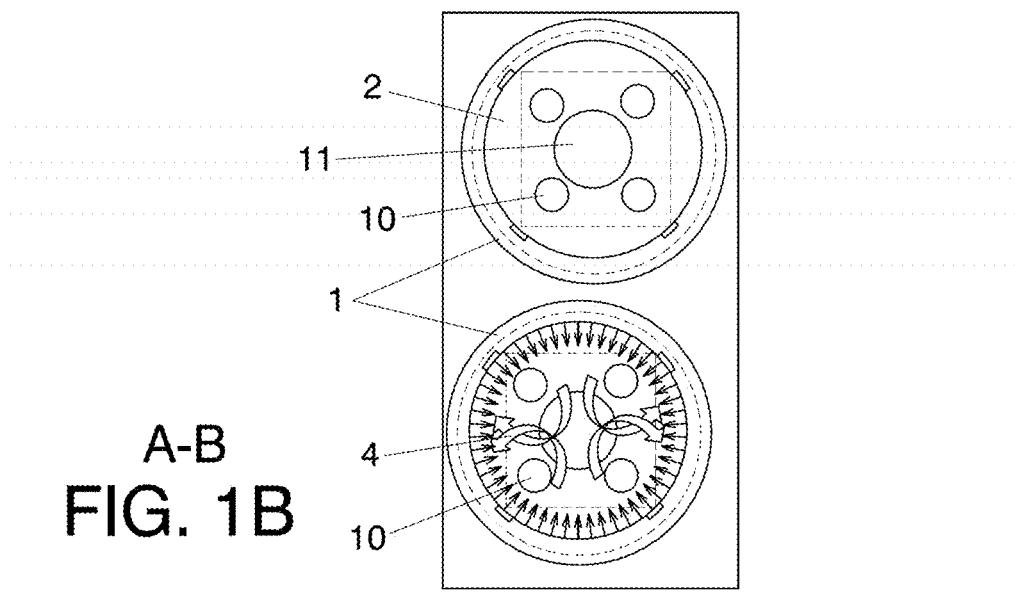
FIG. 1B shows a front view of section AB in a state prior to (at the top) and during (at the bottom) the activation of the cleaning process.

In one embodiment, the cleaning fluid (4) will preferably comprise pressurized air (5) to which more or less cleaning fluid (6) of any type can be added for the purpose of returning transparency and clarity to the field of view (33) of the camera. FIG. 1B depicts a front view corresponding to section AB of FIG. 1A in which a state prior to (at the top) and during (at the bottom) the activation of the cleaning process by means of the cleaning fluid (4), in which the energy scan effect produced by the cleaning fluid (4) when it is sprayed by means of the diffusing element (1) onto the transparent closure (2) has been depicted.

FIG. 1A further shows that the connection of the casing (7) is joined internally at its rear part so as to not form projections to a lower sector (31) of a centering element (22) having a double bend in a central portion.

Figure 2A:
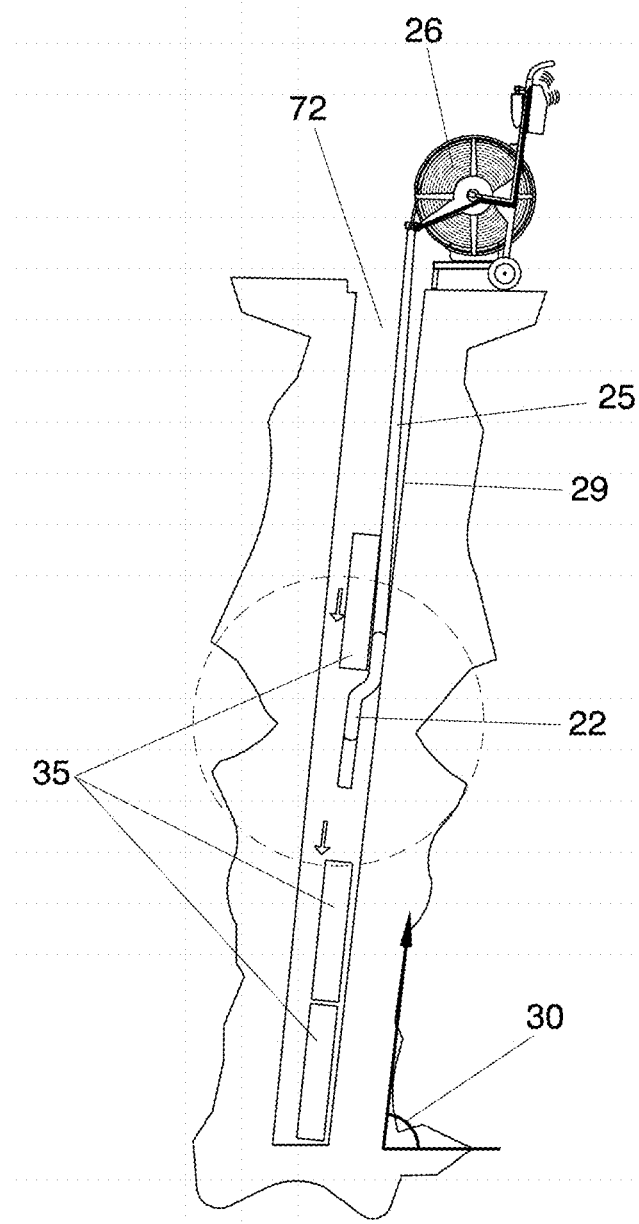
FIG. 2A schematically shows a general view of the working of the system of the invention during a process for loading explosives in a borehole.

FIG. 2A shows a general view of a borehole inspection system according to the invention during a process for loading explosives (35) in a borehole (72). The tubular casing (7) which houses the image capturing means (9), connected to the lower end of the doubly curved centering element (22), connected at its upper end to a tubular conduit (25) partially wound on a winding reel (26) on the surface, can be seen inside the borehole (72). The wiring and conduits necessary for illumination, image capture and the cleaning fluid supply, are protected and located inside the flexible tubular conduit (25) in the form of a hose, which can be a semi-rigid type, its diameter being similar to that of the tubular casing (7) to avoid projections which lead to problems of snagging, or a flat-type, not depicted in the drawing, in which case the diameter is not altogether cylindrical, except that it swells with air during the inspection process. In any case, a tubular conduit (25) having a nominal diameter similar to that of the casing (7) is chosen to meet the same principle that reduces problems of snagging.

The tubular conduit (25) of the semi-rigid hose type or very longitudinally flexible tube allows being wound on a reel (26), which is the most comfortable and natural manner of storing the equipment. This type of tubular conduit (25) has certain advantages:

- Its nominal diameter can be similar to that of the tubular casing (7), without projections, thus minimizing snagging, as previously mentioned.
- Its certain transverse rigidity better protects the wiring and conduits for transmitting image, light and cleaning fluid.
- In the event of snagging, its certain longitudinal rigidity (more pronounced in the case of flexible tubes) allows an alternating push-pull movement which is often sufficient to solve the problem of snagging. This would not be possible with elements lacking that certain longitudinal rigidity, such as normal cables typically incorporated in inspection cameras of the prior art, for example.
- It can be adapted to the irregularities and slight curvatures or deviations of the borehole.
- The certain torsional rigidity prevents the occurrence of uncontrolled rotations of the captured images from inside the borehole, which are very typical when a cable is used for suspending, powering and receiving video images.

Figure 3:
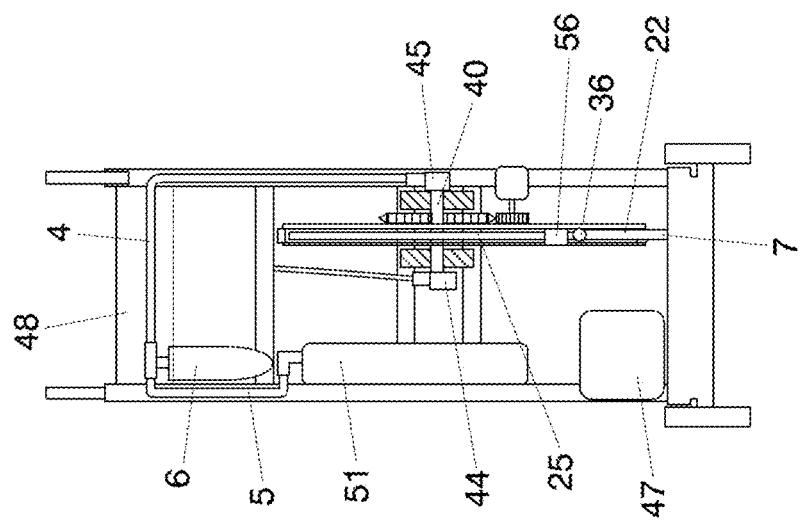
FIG. 3 shows a side and front view of the different elements assembled on a chassis in one embodiment of the system of the invention.
Figure 3:
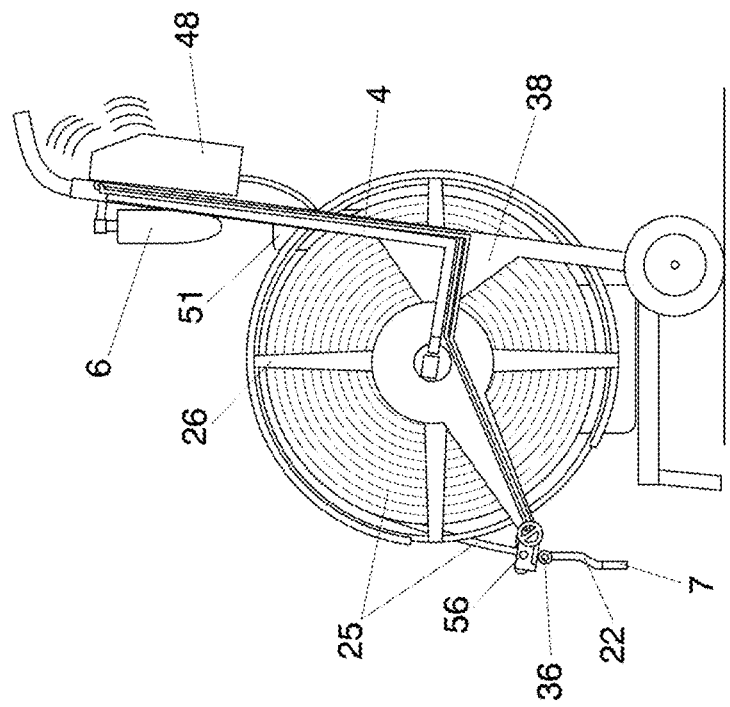
Figure 5:
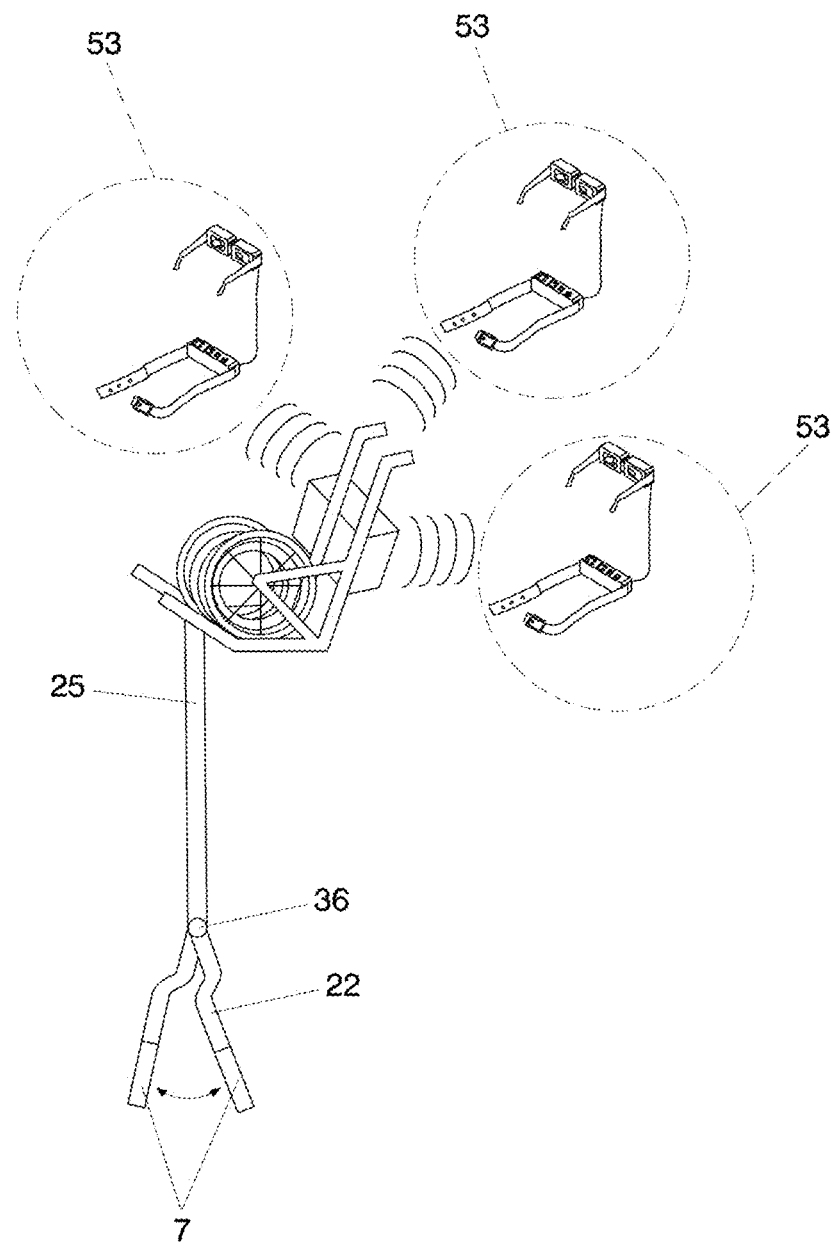
FIG. 5 schematically shows the main elements of the system of the invention, namely, the self-cleaning system, the centering system, and the wireless reception system based on autonomous equipment according to a preferred embodiment.

However, this type of conduit may have a certain curved shape memory (since it is usually wound on a reel, as is seen in FIGS. 2A, 3 and 5) which can jeopardize the centering action of the tubular conduit (25). This drawback can be solved by intercalating a rectifying element (36) between the centering element (22) and the tubular conduit (25) allowing a certain flat rotation, such that it rectifies, with that flat rotation, the possible unwanted curvature of the tubular conduit (25), making the inspection device independent to a certain extent from shape memories of the tubular conduit (25) independent. The rectifying element (36) could be, for example, a short sector of a flat hose which easily allows being bent in the longitudinal direction, rectifying an unwanted curvature memory of the tubular conduit (25).

Though not being depicted in the drawings, the tubular conduit (25) could alternatively be a flat-type hose if, for example, a tubular body with certain rigidity is used as an inner conduit for the cleaning fluid supply, or for the wiring to provide it with some of the advantages described for semi-rigid hoses. For example, this would allow pushing and pulling on the hose given the certain rigidity of the body located in the flat hose, to overcome any problem of snagging. The flat hose, advantageously, is naturally seated on the supporting wall of the borehole, without the tendency to form spirals given its certain flatness, favoring the erect position of the lower sector (31) of the centering element. The rectifying element (36) allowing certain flat rotation would not be necessary with a flat tubular conduit (25), because when the tubular conduit (25) bears a certain weight, it easily loses the tendency to curve.

The centering element (22) is deformable under the action of a stress (for example, the passage of an explosive cartridge), being able to lose the double curvature and resembling a rectilinear tubular body similar to the tubular conduit (25) in the depicted embodiment, thus preventing any projection which puts the device at the risk of being snagged, but with shape memory to recover the original shape and location once the stress ends. It can be observed that in the natural double bend situation, the upper sector (28) of the centering element (22) is substantially in contact with the wall of the borehole (29), and the lower sector (31) of the centering element, connected to the tubular casing (7), is kept erect and substantially centered in the borehole (72). The centered position is favored by the certain torsional rigidity of the tubular conduit (25) connected without any projection which puts the system at the risk of snagging. In an embodiment not depicted, the centering element is coupled, preventing the formation of projections, in a longitudinal sector of the tubular conduit (25), the centering element containing the tubular conduit (25) in that sector, or the centering element being contained in the tubular conduit (25) in that sector, such that in either of the two cases that sector of tubular conduit (25) acquires the characteristic shape of the coupled centering element.

Figure 2B:
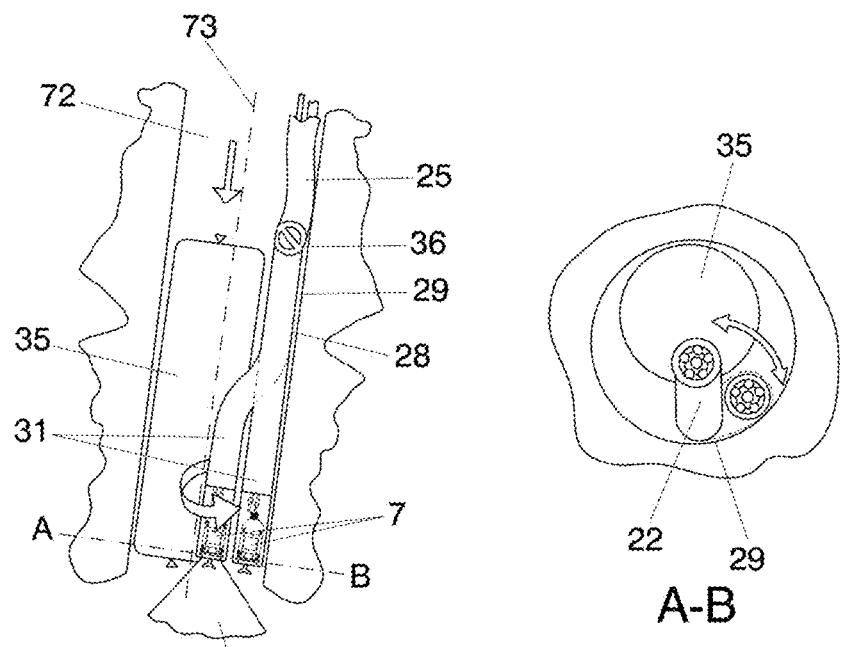
FIGS. 2B and 2C show the positioning of the centering element during the passage of an explosive cartridge.
Figure 2C:
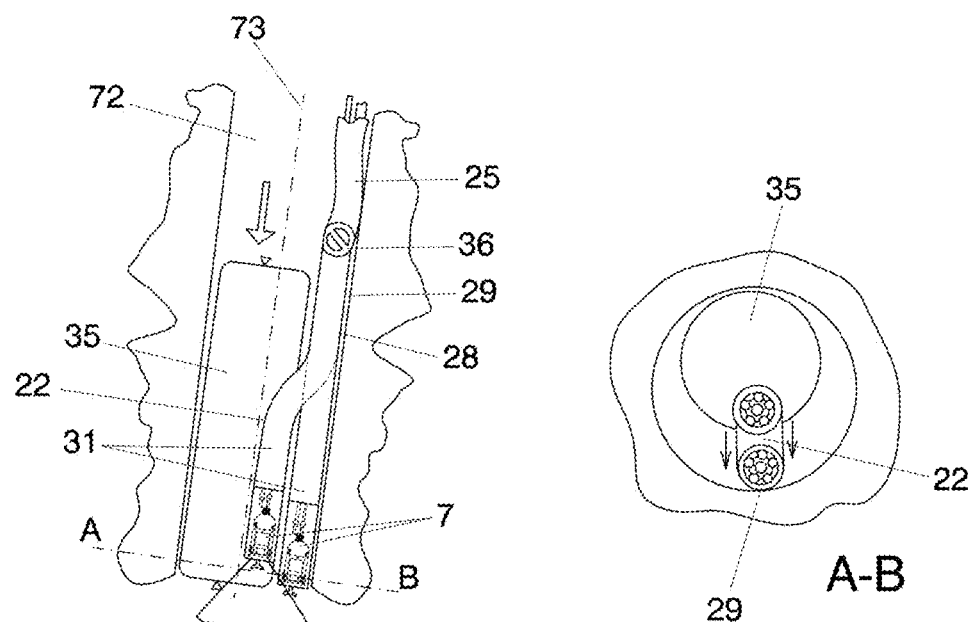

FIGS. 2B and 2C depict an enlarged view of the positioning of the centering element (22) in an equilibrium situation, with its upper sector (28) substantially supported on the slip plane (29) of the borehole and its lower sector (31) substantially centered in the borehole, erected close to the axis of symmetry (73) of the borehole, as a result of the double curve; and in a situation in which an explosive cartridge (35) traverses the position of the centering element (22) in the borehole (72). When an explosive cartridge (35) traverses the position of the centering element (22) in the borehole it deforms it either by means of a partial rotation of the lower sector (31), as depicted in FIG. 2B, which causes a torsional deformation of the tubular conduit (25), which will tend to equilibrate itself, returning to its position when the cartridge (35) passes, or by longitudinally deforming while the cartridge (35) passes, as shown in FIG. 2C, the equilibrium position being recovered once the cartridge goes beyond the position of the centering element (22), given the aforementioned features thereof. Front views of section AB in both cases are also depicted, showing the deformation and/or the movement of the centering element (22) during the passage of the cartridge (35).

In an advantageous embodiment, fiber optic conduits can be used as image capturing means (9) and illumination means (10), responsible for illuminating, transmitting light from the surface and for returning the image for processing, from inside the borehole to the surface, said fiber optic conduits being protected in their front part by the transparent closure (2) which would be the element object of the self-cleaning action.

The greatest diameter of the elements introduced in the boreholes, which would generally correspond to that of the tubular conduit (25), will preferably be equal to or less than approximately 30% of the diameter of the borehole, which would allow the device to stay inside the borehole while the explosives are introduced in their cartridge format.

FIG. 3 shows side and front views of a possible configuration of the system, in which a winding reel (26) designed, for example, to operate by drawing in and letting out in one and the same winding plane (spiral type winding) the entire length of the tubular conduit (25), can be seen, the tubular casing (7) which houses the image capturing means (9), the centering element (22) and the rectifying element (36) which allows rectifying a certain curvature memory that can affect the tubular conduit (25), thus facilitating the introduction of the inspection device in the borehole.

In a preferred embodiment, the borehole inspection system comprises the means necessary for making the signal of the images reach, first through the wiring or conduits located along the borehole inside the tubular conduit (25) supporting the equipment, to a signal processing element and wireless transmitter (48) located on the surface, able to send by aerial means the signal consisting of the images and the numerical value of the depth at which the device is located inside the borehole. The value of the depth is generated by means of a depth indicator (57), in this embodiment a meter counting device (57) with reset, located in a multipurpose element (56) described below. The composite signal (image-depth) can be sent to one or several wireless receivers (53) to be displayed.

In a preferred embodiment, the wireless receiver (53) comprises a video unit with basic functions (play, record fast forward and rewind) and an element for viewing the images (54), preferably of the binocular glasses type for contemplating and analyzing the video images, while at the same time avoiding the usual problems with displays in areas in the open air, such as glare from the sun, dirt, rain, giving the operators considerable mobility and autonomy.

Figure 4:
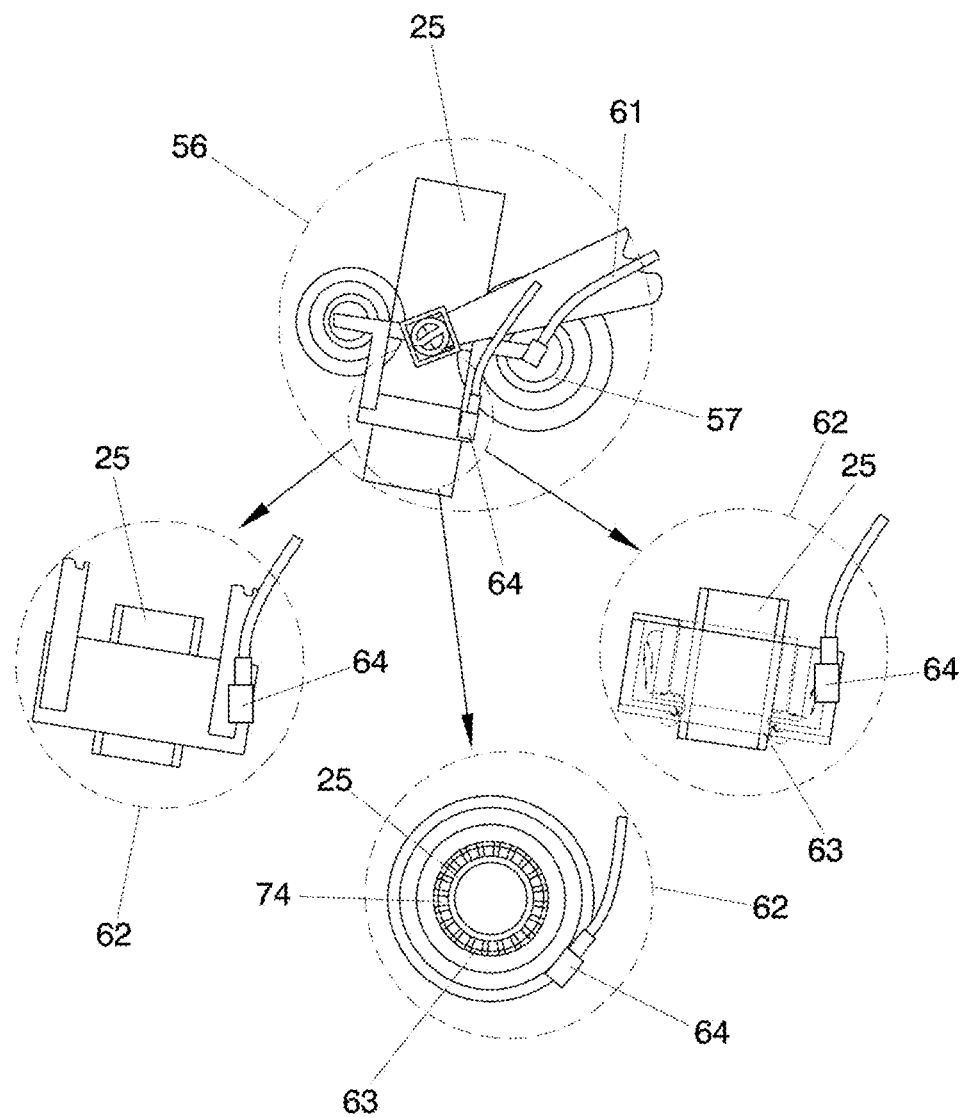
FIG. 4 shows two side views and a front view of details of the multipurpose device described in the specification which houses a depth indicator system and a cleaning device.

FIG. 4 shows details of the multipurpose element (56), incorporating the meter counting device (57) with a reset function and a cleaning device (62) for cleaning the remaining mud or even explosive adhered to the tubular conduit (25). The meter counting system (57) detects and measures the linear meters, either based on a system of pulleys and on the rolling without slip generated in said pulleys by the tubular conduit (25) upon its passage while it is let out or drawn in, or alternatively by means of a detection system for detecting certain elements (not depicted in the drawings), for example magnetized rings or metal rings, located in a spaced manner and at a known distance, inside the tubular conduit (25), such that upon their passage they generate a signal equivalent to the known distance between said equidistant elements. The meter counting element (57) can send its reading through conventional means, for example a cable (61), to a signal processing element and wireless transmitter (48) and from there to one or several wireless units (53) for viewing them together with the video image.

The second function of the multipurpose element (56) would be to clean, during the drawing-in phase, the remaining dirt and eventually the explosives that have impregnated the flexible tubular conduit (25). To that end, it comprises a cleaning element (62), assembled at the outlet of the multipurpose element (56), configured like an annular body through which the flexible tubular conduit (25) circulates with certain friction, such friction being like that which would be caused, for example, by brushes or a spongy body (74) in the entire periphery, sweeping the remaining dirt during the phase for drawing in the flexible tubular conduit (25). Alternatively or complementarily, the cleaning fluid (4) can be used to clean the flexible tubular conduit (25), in which case the cleaning element (62) could comprise a thin diffusing groove (63) and a small intake (64) through which the cleaning fluid (4) would circulate on demand through a conduit. This process can be controlled independently from the cleaning of the transparent closure (2), such that both cleaning processes are autonomous.

The multipurpose device (56) depicted can also work as a guiding element during the winding of the flexible tubular conduit (25), since its location in the winding plane by means of a support solidly joined to the chassis (38) facilitates the flexible tubular conduit (25) being guided into the reel (26).

FIG. 4 also includes enlargements in detail of several elements of an embodiment of the cleaning element (62) in two side views and a front view, in which the intake (64), the diffusing groove (63), the brush type element (74) removing the mud remains or even explosives adhered to the flexible tubular conduit (25) are distinguished.

Another advantageous embodiment of the borehole inspection device describes a winding reel (26) and two rotating adaptors (44, 45) assembled at both ends of a rotation shaft (40), depicted in FIG. 3, or alternatively at a single end concentrically (not depicted in the drawings), which allow supplying at the same time the means necessary for capturing the images and the means necessary for cleaning the transparent closure element (2), while the tubular conduit (25) is being pulled out and drawn in.

FIG. 5 schematically depicts the use configuration of the borehole inspection system, in which there is a signal processing element and wireless transmitter (48) located on the surface and one or several individual receivers (53) which the users will wear with the possibility of viewing the images while loading explosives, recording and playing from the individual unit itself.

Figure 6:
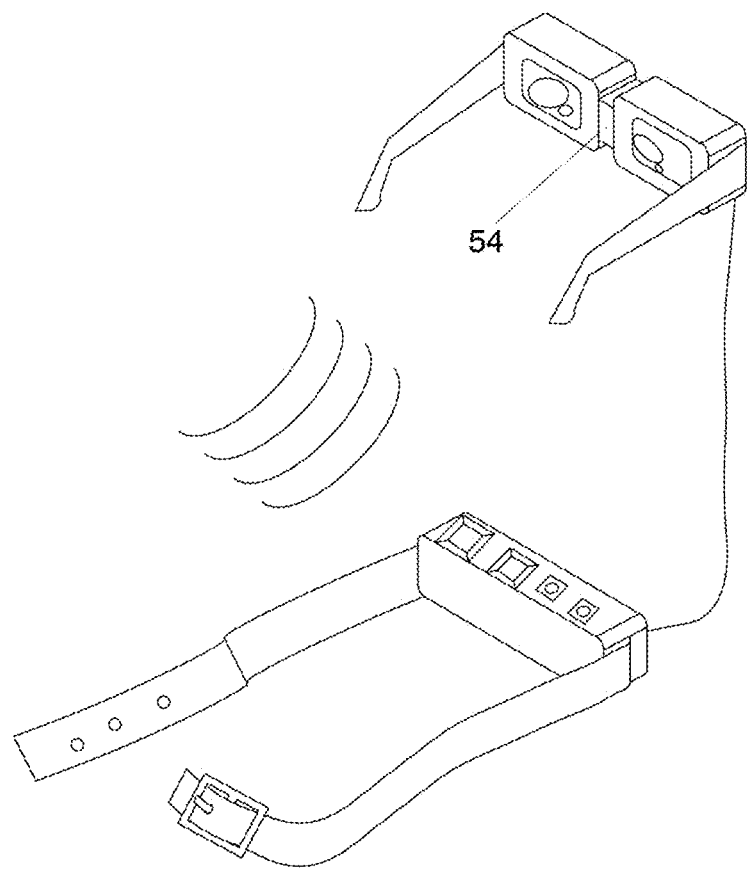
FIG. 6 shows an enlarged detail of an individual glasses-type wireless receiver with the capacity to receive the video signal and the information about the meters of depth and composing them into a video image for viewing them.

FIG. 6 shows an enlarged detail of an individual wireless receiver (53) with the capacity to receive the video signal and the information about the meters of depth and composing them into a video image which will be viewed by means of glasses (54), avoiding problems of reflections, dirt, etc.

In the embodiment of the drawing, a power source (47) provides energy to the image capturing means (9) and to the illumination means (10), to the compressed air unit (51) responsible for generating pressurized air (5), the main component of the cleaning fluid (4), and to the signal processing element and wireless transmitter (48) located on the surface, which receives the video signal through the cable (13) and sends it over the air to the individual wireless receivers (53) which in turn transform the video signal into images in the viewing glasses (54) that the users wear in the blast.

The device of the invention allows cleaning from the surface the transparent closure (2) of the image capturing means, centering the field of view (33) in the section of the borehole without having to use elements which form projections and viewing in at least one video receiver (53), preferably a wireless receiver of the viewing glasses (54) type, the images and the depth at which the equipment is located, all by means of the on-demand supply of a cleaning fluid (4), which may or may not additionally incorporate a cleaning liquid (6) such that the transparent closure (2) can be kept clean without needing to extract the equipment to the surface. By means of the previously described centering element (22), a centered field of view (33) of the inside of the borehole is achieved without it involving a projection which causes problems of snagging given the deformable feature of the centering element (22). The system allows the blast operators to contemplate, analyze, record and play, in a novel manner, in viewing wireless binoculars (54) and in the video unit with the basic functions of a video player (playing, pausing, recording, etc), the video images of the inside of the borehole which include the information of the depth at which the inspection device (7) is located, which has previously been calculated by a meter counting element (57) and added to the video signal by a signal processing element and wireless transmitter (48) which, once both signals (video and depth) are processed, integrates them or adds them and transmits them, preferably wirelessly, to the individual wireless receivers (53) which in turn transform the video signal into images in the viewing glasses (54) that the users would wear in the blast.

The method for loading of the invention is based, in a novel manner, on performing a thorough and systematic real time follow up of the loading of the explosive in boreholes since an inspection device enabling a rapid self-cleaning without needing to extract it from the borehole can be arranged, which allows maintaining a centered view of the borehole at all times, and which does not have pronounced projections, so as to prevent the unwanted problems of equipment getting snagged in the boreholes.

In an advantageous embodiment, the method of the invention comprises viewing, while loading an explosive in the borehole, the images of loading the borehole together with a value indicative of the depths of the borehole associated with the captured images in a viewing system comprising wireless binocular glasses. For this purpose it would use the means necessary for capturing the images of the process for loading explosives and the means for incorporating in said images the value of the depth of the borehole at which the captured images correspond. The operators are thus able to use a novel video viewing system, based on using wireless glasses (54), whereby being able to contemplate and analyze, record and play back the images of what takes place, eliminating the typical drawbacks of conventional displays when they are viewed in the open air or outside, such as reflections, the glare of the sun, dirt, rain.

Advantageously, the novel wireless configuration described for the inspection and viewing in real time of the inside of a borehole while loading the explosive allows the user to view, in the images substantially enlarged by the optical effect inherent to the glasses system, the actual depth at which the device is located at all times and therefore any incidence that it detects. This advantage is maximum when the images have been recorded and allow the users, in later playbacks, to perfectly locate the incidences detected at their respective depth. To that end, the wireless units (53) which will receive the video signal and reading of the meter counting device are provided with basic camera/video functions: live, record, play, pause, fast forward, rewind and stop.

The invention claimed is:

1. A borehole inspection device comprising
   (a) a centering element (22) having a first end and a second end, wherein the centering element comprises a double bend between the first end and the second end, wherein the centering element has shape memory such that the centering element loses the double bend when being longitudinally deformed under the action of a force, the first end being provided to remain substantially in contact with the wall of the borehole and the second end being provided to remain substantially centered in the borehole when not being deformed,
   (b) a tubular casing (7) attached to the second end of the centering element (22), said tubular casing (7) comprising
      (i) illumination means (10) and image capturing means (9), housed in the casing (7), (ii) at least one circulation duct (16) for a fluid (4), (iii) a diffusing element (1) suitable for spraying the pressurized fluid (4) circulating through the at least one circulation duct (16) onto a transparent closure (2) allowing the illumination and the image capture through it, and (c) a flexible tubular conduit (25), with torsional rigidity attached to the first end of the centering element (22).

2. The borehole inspection device according to claim 1, wherein the circulation duct (16) is an annular duct.

3. A borehole inspection system comprising a borehole inspection device according to claim 1 wherein the tubular conduit (25) is a flexible conduit, with torsional rigidity, which internally houses fluid supply means and data transmission means, said inspection system lacking projections in the connections of the elements intended for being introduced in the borehole.

4. The borehole inspection system according to claim 3, wherein the centering element (22) is either longitudinally coupled to the tubular conduit (25) partially or completely containing it, or partially or completely contained in it.

5. The borehole inspection system according to claim 3, wherein the centering element (22) is connected to the tubular conduit (25) by a rectifying element (36) which allows the part of the borehole inspection system located downstream from said rectifying element (36) to freely rotate about an axis substantially perpendicular to the axis of the borehole.

6. The borehole inspection system according to claim 3, wherein the tubular conduit (25) internally houses power supply means.

7. The borehole inspection system according to claim 3, wherein the illumination means (10), the image capturing means (9) and the data transmission means are fiber optic conduits.

8. The borehole inspection system according to claim 3, comprising a depth indicator (57) for providing a value indicative of the depth at which the borehole inspection device is located inside the borehole.

9. The borehole inspection system according to claim 3, comprising a wireless emitter for receiving a video signal of the image capturing means (9) and sending it to at least one wireless receiver (53) which transforms the video signal into images for viewing them in at least one viewing system (54).

10. The borehole inspection system according to claim 7, comprising means for composing the captured images with the value indicative of the depths of the borehole associated with the images and a viewing system comprising wireless binocular glasses (54) for viewing said composition.

11. The borehole inspection system according to claim 3, comprising a cleaning device (62) formed as an annular body surrounding the tubular conduit (25), providing friction against the passage of the tubular conduit (25) suitable for sweeping up the remaining dirt during the drawing-in phase.

12. The borehole inspection system according to claim 3, comprising a winding reel (26) and respective rotating adaptors (44, 45) for respectively supplying the data transmission means and the fluid supply means.

13. A method for loading explosives in a borehole comprising the following steps:
inserting a borehole inspection device of a borehole inspection system according to claim 3 in a borehole;
loading an explosive cartridge in the borehole; and
capturing images from inside the borehole using the borehole inspection system while loading an explosive cartridge in the borehole.

14. The method for loading explosives in a borehole according to claim 13, which comprises performing at least one cleaning operation onto the transparent closure (2) of the borehole inspection device located inside the borehole.

15. The method for loading explosives in a borehole according to claim 14, which comprises viewing, while loading an explosive cartridge in the borehole, the images of loading the borehole together with a value indicative of the depths of the borehole associated with the captured images in a viewing system comprising wireless binocular glasses (54).

16. The borehole inspection device according to claim 1, wherein the longitudinal deformation of the centering element causes the centering element to resemble a rectilinear tubular body similar to the tubular conduit (25).

17. The borehole inspection device according to claim 1, wherein the double bend comprises two bends in opposite directions.

* * * * *